US010278977B2

(12) United States Patent
Bäckström et al.

(10) Patent No.: US 10,278,977 B2
(45) Date of Patent: May 7, 2019

(54) METHODS FOR TREATING HYPERSOMNOLENCE

(71) Applicant: Umecrine Cognition AB, Solna (SE)

(72) Inventors: Torbjörn Bäckström, Umeå (SE); Magnus Doverskog, Stockholm (SE); Maja Johansson, Vannas (SE); Pontus Wasling, Göteborg (SE)

(73) Assignee: Umecrine Cognition AB, Solna (SE)

( * ) Notice: Subject to any disclaimer, the term of this patent is extended or adjusted under 35 U.S.C. 154(b) by 0 days.

(21) Appl. No.: 15/613,539

(22) Filed: Jun. 5, 2017

(65) Prior Publication Data

US 2017/0348323 A1 Dec. 7, 2017

Related U.S. Application Data

(60) Provisional application No. 62/346,104, filed on Jun. 6, 2016.

(51) Int. Cl.
*A61K 31/568* (2006.01)
*A61K 31/04* (2006.01)
*A61K 31/015* (2006.01)

(52) U.S. Cl.
CPC .......... *A61K 31/568* (2013.01); *A61K 31/015* (2013.01); *A61K 31/04* (2013.01)

(58) Field of Classification Search
CPC ............................ A61K 31/565; A61K 31/568
USPC ....................................................... 514/182
See application file for complete search history.

(56) References Cited

U.S. PATENT DOCUMENTS

| 2,713,061 | A | 7/1955 | Kathol |
| 3,173,932 | A | 3/1965 | Contrail et al. |
| 6,596,885 | B2 | 7/2003 | Claussner et al. |
| 6,852,710 | B2 | 2/2005 | Rao et al. |
| 8,580,983 | B2 | 11/2013 | Backstrom et al. |
| 8,853,190 | B2 | 10/2014 | Backstrom et al. |
| 9,200,028 | B2 | 12/2015 | Backstrom et al. |
| 2011/0028418 | A1 | 2/2011 | Parker et al. |

FOREIGN PATENT DOCUMENTS

| FR | 1 463 755 A | 7/1966 |
| WO | 94/27608 A1 | 12/1994 |
| WO | 99/45931 A1 | 9/1999 |
| WO | 2003/059357 A1 | 7/2003 |
| WO | 2009142594 A1 | 11/2009 |
| WO | 2015114308 A1 | 8/2015 |
| WO | 2015/160766 A1 | 10/2015 |

OTHER PUBLICATIONS

Bengtsson et al., Isoallopregnanolone antagonize allopregnanolone-induced effects on saccadic eye velocity and self-reported sedation in humans Psychoneuroendocrinology, 2015, 52, 22-31, Accepted Oct. 31, 2014.
Billiard et al., Idiopathic hypersomnia, Sleep Medicine Reviews, 29, 2016; pp. 23-33, Accepted Aug. 24, 2015.
Dauvilliers et al. Absence of n-Aminobutyric Acid-A Receptor Potentiation in Central Hypersomnolence Disorders, Ann. Neurol., 2016. 80(2): pp. 259-268 Accepted Jun. 7, 2016.
Dauvilliers, Y et al. Reply to "Rigor, Reproducibility and In Vitro CSF Assays: The Devil in the Details" Ann Neurol, Jun. 2017; doi:10.1002/ana.24939 vol. 81, No. 6.
Johansson et al., GABAA receptor modulating steroid antagonists (GAMSA) are functional in vivo, J. Steroid Biochem. Mol. Biol. 2016, 160, 98-105, Accepted Oct. 25, 2015.
Johansson et al., GR3027 antagonizes GABAA receptor-potentiating neurosteroids and restores spatial learning and motor coordination in rats with chronic hyperammonemia and hepatic encephalopathy, Am J Physiol Gastrointest Liver Physiol 309: G400-G409, Jun. 29, 2015.
Johns; A New Method for Measuring Daytime Sleepiness: The Epworth Sleepiness Scale, Sleep, 14(6), pp. 540-545, Accepted Jul. 1991.
Kelty et al., Use of subcutaneous flumazenil preparations for the treatment of idiopathic hypersomnia: a case report Journal of Psychopharmacology, 2014, 28(7), 703-706, Nov. 19, 2014.
Khan et al., Focus on the Narcolepsies and Idiopathic Hypersomnia, Contemporary Reviews in Sleep Medicine, 2015; 148 (1): pp. 262-273, Accepted Jan. 7, 2015.
Moody et al., Rigor, Reproducibility and in vitro CSF assays: The Devil in the Details Ann. Neurol, June;81(6):904-907. doi: 10.1002/ana.24940. Epub Jun. 1, 2017.
Rye et al. Modulation of Vigilance in the Primary Hypersomnias by Endogenous Endogenous Enhancement of GABA A Receptors Sci. Transl. Med., Nov. 21, 2012; 4:161.
Saini et al., Hypersomnia Evaluation, Treatment, and Social and Economic Aspects Sleep Med Clin, Mar. 2017, 12, 47-60.
Singh et al., The Prevalence of Multiple Sleep-Onset REM Periods in a Population-Based Sample, Sleep, Jul. 1, 2006, 29(7), pp. 890-895.
Sowa et al., Idiopathic Hypersomnia and Hypersomnolence Disorder: A Systematic Review of the Literature Phsychosomatics, Mar./Apr. 2016, 57(2), pp. 152-164.
Trotti et al., Improvement in daytime sleepiness with clarithromycin in patients with GABA-related hypersomnia: Clinical experience, Journal of Psychopharmacology, Nov. 18, 2014, 28 (7), 697-702.
Vernet and Arnulf; Idiopathic Hypersomnia with and without Long Sleep Time: A Controlled Series Jun. 1, 2009; Sleep, 32(6); pp. 753-759.
Wang et al., 3 b,Hydroxypregnane Steroids Are Pregnenolone Sulfate-Like GABAA Receptor AntagonistsJ. Neuro. Sci. May 1, 2002, 22(9), 3366-75.
Wang et al., The inhibitory effects of allopregnanolone and pregnanolone on the population spike, evoked in the rat hippocampal CA1 stratum pyramidale in vitro, can be blocked selectively by epiallopregnanolone, Acta. Physiol. Scand. Jun. 3, 2000, 169, 333-341.

*Primary Examiner* — Barbara P Badio
(74) *Attorney, Agent, or Firm* — McCarter & English, LLP; Xin Zhang; Steven G. Davis

(57) ABSTRACT

There is provided a method of treatment of hypersomnolence comprising administering the steroidal compound 3α-ethynyl-3β-hydroxy-5α-androstan-17-one oxime, or a pharmaceutically acceptable salt thereof, to a subject in need of such treatment.

10 Claims, No Drawings

METHODS FOR TREATING HYPERSOMNOLENCE

RELATED APPLICATIONS

This application claims the benefit of the filing date under 35 U.S.C. § 119(e), of U.S. Provisional Application No. 62/346,104, filed on Jun. 6, 2016, the entire content of which is incorporated herein by reference.

FIELD OF THE INVENTION

The present invention relates to methods for the treatment of hypersomnolence, such as idiopathic hypersomnia, and/or methods for promoting wakefulness, comprising administering a specific steroid compound to a subject in need of such treatment.

BACKGROUND OF THE INVENTION

The listing or discussion of an apparently prior-published document in this specification should not necessarily be taken as an acknowledgement that the document is part of the state of the art or is common general knowledge.

Hypersomnolence is characterized by severe daytime sleepiness, which is present despite normal quality and timing of nocturnal sleep. Recent reclassification (ISCD-3) distinguishes between three main subtypes: narcolepsy type 1 (with cataplexy), narcolepsy type 2 (without cataplexy), and idiopathic hypersomnia (IH; with or without long sleep time) (Khan and Trotti 2015; *Contemporary Reviews in Sleep Medicine*, pp. 262-273).

Excessive Daytime Sleeping (EDS) is the principal feature of the central disorders of hypersomnolence. EDS is defined as the inability to stay awake and alert during major waking episodes of the day, resulting in periods of irrepressible need for sleep or unintended lapses into drowsiness or sleep. The Epworth Sleepiness Scale (ESS) is widely used in the field of sleep medicine as a subjective measure of a patient's sleepiness (Johns 1991; *Sleep,* 14(6), pp. 540-545). The total ESS score can range from zero to 24 with higher scores correlating with increasing degrees of sleepiness. A score greater than 10 is consistent with excessive sleepiness. The mean ESS score is approximately six among healthy adults, compared to 16 or greater among patients with narcolepsy or idiopathic hypersomnia.

Idiopathic hypersomnia (also known as idiopathic hypersomnolence) is a sleep disorder that is characterized by chronic excessive daytime sleepiness (daily periods of irrepressible need to sleep or daytime lapses into sleep) and often difficulty waking up from nocturnal sleep or daytime naps (sleep inertia). Unlike narcolepsy, spontaneous remission has been reported in 14% to 25% of patients with IH (Vernet and Arnulf 2009; *Sleep,* 32(6); pp. 753-759). IH is associated with several somatic symptoms and comorbid conditions (Sowa et al. *Phsychosomatics,* 2016, 57(2), pp. 152-164). Memory difficulties (79%), attentional difficulties (55%), chronic headache (52.8%), and excessive sweating (34.7%) are particularly prominent and depression is present in 15.1% of patients. The condition is disabling, sometimes even more so than narcolepsy type 1 or 2. (Billiard and Sonka; *Sleep Medicine Reviews,* 29, 2016; pp. 23-33). Initially, complications of idiopathic hypersomnia may appear similar to those of narcolepsy type 1 or 2, including poor performance at school and work, sleep during recreational activities and a higher incidence of car accidents. However, some idiopathic hypersomnia patients experience unique and often debilitating complaints including the absence of benefit from nocturnal sleep and daytime naps to the extent that they never feel refreshed, difficulty in awakening and resistance to stimulant medications (Singh M, Drake C L, Roth T; *The prevalence of multiple sleep-onset REM periods in a population-based sample; Sleep,* 2006, 29(7), pp. 890-895). These issues can make it difficult to pursue a normal lifestyle and put pressure on the sufferer's work and family relationships.

There is some debate in the literature regarding the underlying causes of hypersomnolence. Rye et al. (*Sci. Transl. Med.,* 2012; 4:161) have suggested that a naturally-occurring substance in cerebrospinal fluid (CSF) augments inhibitory GABA signaling, thus revealing a new pathophysiology associated with excessive daytime sleepiness. However, Dauvilliers et al. (*Ann. Neurol.,* 2016. 80(2): pp. 259-268, concluded that CSF $GABA_A$ receptor activity does not appear to be a useful biomarker for assessing the etiology or severity of centrally-mediated hypersomnolence disorders, including idiopathic hypersomnia.

More recently, Moody, O. A., et al. (*Ann. Neurol,* 2017, doi: 10.1002/ana.24940) have refuted the findings of Dauvilliers et al. and have demonstrated reproducible $GABA_A$ receptor enhancement in 32 novel CSF samples. Moody et al. suggest that Dauvilliers and colleague's inability to do so is attributable to flaws in their experimental design. However, Dauvilliers, Y et al. (*Ann Neurol,* 2017; doi:10.1002/ana.24939), have again disagreed with the findings of Moody et al., and published a defence of their study and conclusions.

Thus, the etiology of hypersomnolence disorders, such as idiopathic hypersomnia, remains unclear.

This notwithstanding, treatments that act as GABA antagonists, e.g. flumazenil and clarithromycin, have shown some promise for the treatment of idiopathic hypersomnia, although their use is still experimental (see, for example Kelty et al., *Journal of Psychopharmacology,* 2014, 28(7), 703-706 and Trotti et al., *Journal of Psychopharmacology,* 2014, 28(7), 697-702).

US 2011/0028418 discloses a method of treating $GABA_A$ receptor mediated hypersomnia and excessive sleepiness associated with $GABA_A$ receptor mediated hypersomnia by using flumazenil.

WO 2015/160766 discloses a method of treating hypersomnia by administering $GABA_A$ chloride channel blockers such as pentylenetetrazole (PTZ), bilobalide (BB), penicillin and ginkolide B.

There are currently no approved therapies for idiopathic hypersomnia, although several generic treatments are used as compassionate medications (off-label), such as modafinil (branded under e.g. the trademark PROVIGIL® ((modafinil) and amphetamine derivatives, which primarily are FDA/EMA approved wake-promoting narcolepsy medications. Sodium oxybate (branded under e.g. the trademark XYREM® (sodium oxybate)) is also used off-label as a second/third line treatment. However, the treatment options currently available for idiopathic hypersomnia are often unsatisfactory, with suboptimal efficacy, troublesome side effects, development of drug tolerance, and inconvenience. There is therefore a need for a safe and effective drug for the treatment of idiopathic hypersomnia.

3α-ethynyl-3β-hydroxy-5α-androstan-17-one oxime is disclosed in WO 2008/063128 and is known to act as an antagonist to the positive allosteric modulation of $GABA_A$ receptors by endogenous neurosteroids including allopregnanolone and tetrahydrodeoxycorticosterone (THDOC).

This compound is disclosed for the treatment of hepatic encephalopathy in WO 2015/114308.

DESCRIPTION OF THE INVENTION

The present invention is directed towards the compound 3α-ethynyl-3β-hydroxy-5α-androstan-17-one oxime for the treatment of hypersomnolence, and disorders related thereto.

Methods of Treatment

In an aspect of the invention, there is provided a method for the treatment of hypersomnolence comprising administering a therapeutically effective amount of 3α-ethynyl-3β-hydroxy-5α-androstan-17-one oxime,

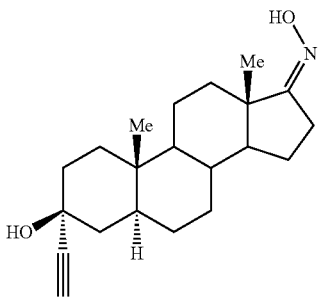 [SMILES: C#C[C@]1(O)CC[C@]2(C)C3CC[C@]4(C)/C(=N\O)CCC4C3CC[C@H]2C1]

or a pharmaceutically acceptable salt thereof, to a subject in need of such treatment.

The compound 3α-ethynyl-3β-hydroxy-5α-androstan-17-one oxime and its synthesis, is disclosed in the applicant's published application WO 2008/063128.

For the avoidance of doubt, 3α-ethynyl-3β-hydroxy-5α-androstan-17-one oxime, and pharmaceutically acceptable salts thereof, may be referred to as "compounds of the invention".

Unless indicated otherwise, all technical and scientific terms used herein have the same meaning as commonly understood by one of ordinary skill in the art to which this invention pertains.

Preferences and options for a given aspect, feature or parameter of the invention should, unless the context indicates otherwise, be regarded as having been disclosed in combination with any and all preferences and options for all other aspects, features and parameters of the invention.

Pharmaceutically acceptable salts within the scope of the invention include acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. under reduced pressure, by freeze-drying or by filtration). Salts may also be prepared by exchanging a counter-ion of a compound of the invention in the form of a salt with another counter-ion, for example using a suitable ion exchange resin.

Particular acid addition salts that may be mentioned include carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxy-benzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulphonate salts (e.g. benzenesulphonate, methyl-, bromo- or chloro-benzenesulphonate, xylenesulphonate, methanesulphonate, ethanesulphonate, propanesulphonate, hydroxy-ethanesulphonate, 1- or 2-naphthalene-sulphonate or 1,5-naphthalenedisulphonate salts) or sulphate, pyrosulphate, bisulphate, sulphite, bisulphite, phosphate, monohydrogenphosphate, dihydrogenphosphate, metaphosphate, pyrophosphate or nitrate salts, and the like.

Particular base addition salts that may be mentioned include salts formed with alkali metals (such as Na and K salts), alkaline earth metals (such as Mg and Ca salts), organic bases (such as ethanolamine, diethanolamine, triethanolamine, tromethamine and lysine) and inorganic bases (such as ammonia and aluminium hydroxide). More particularly, base addition salts that may be mentioned include Mg, Ca and, most particularly, K and Na salts.

In certain embodiments, the salt may be the hydrochloride or the sodium salt.

For the avoidance of doubt, 3α-ethynyl-3β-hydroxy-5α-androstan-17-one oxime, and pharmaceutically acceptable salts thereof, may exist as solids, and thus the scope of the invention includes all amorphous, crystalline and part crystalline forms thereof. Where compounds of the invention exist in crystalline and part crystalline forms, such forms may include solvates, which are included in the scope of the invention. Compounds of the invention may also exist in solution.

The present invention also embraces isotopically-labelled 3α-ethynyl-3β-hydroxy-5α-androstan-17-one oxime, and pharmaceutically acceptable salts thereof, which are identical, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Hence, references to 3α-ethynyl-3β-hydroxy-5α-androstan-17-one oxime, or a pharmaceutically acceptable salt thereof, also includes deuterated compounds, i.e. in which one or more hydrogen atoms are replaced by the hydrogen isotope deuterium.

As used herein the term "hypersomnolence" may be understood to indicate a group of disorders characterised by excessive daytime sleepiness, which occurs despite the subject generally experiencing a normal quality and timing of nocturnal sleep. As discussed hereinabove, excessive daytime sleepiness may be defined as the inability to stay awake and alert during major waking episodes of the day, resulting in periods of irrepressible need for sleep or unintended lapses into drowsiness or sleep.

The skilled person will appreciate that hypersomnolence may be assessed and diagnosed, and treatments evaluated, according to a range of scales and/or tests as known in the art.

For example, scales that may be useful include the Stanford Sleepiness Scale (SSS) and the Epworth Sleepiness Scale (ESS). The SSS and the ESS assess a subject's sleepiness according to their self-assessed sleepiness scores at different time points during the day or during different everyday activities. A score of above 10 (for example about 16) on the ESS may indicate symptoms of hypersomnolence in a subject.

Further subjective tests and questionnaires suitable for the assessment of the symptoms of hypersomnia and excessive daytime sleepiness include the Functional Outcomes of Sleep Questionnaire (FOSQ) and the Multidimensional Fatigue Inventory (MFI), and the, clinician-assessed, Clinical Global Impression of Severity and Clinical Global Impression of Change (CGI-S and CGI-C). Self-reported indicia also include self-reported fogginess scores, self-reported mood scores and self-reported sleepiness scores.

Tests that may be useful include the Multiple Sleep Latency Test (MSLT), the Maintenance of Wakefulness Test (MWT) and the Psychomotor Vigilance Task (PVT). For example, it is understood that sleep latency of less than about 8 minutes on the MSLT indicates the presence of excessive daytime sleepiness.

The skilled person will understand that references to the treatment of a particular condition (or, similarly, to treating that condition) take their normal meanings in the field of medicine. In particular, the terms may refer to achieving a reduction in the severity of one or more clinical symptom associated with the condition. For example, in the case of hypersomnolence, the term may refer to achieving a reduction in the daytime sleepiness experienced by a subject (for example, as measured by the tests, scales and questionnaires listed above).

As used herein, references to subjects will refer to a living subject being treated, including mammalian (e.g. human) patients, and as such subjects may also be referred to as patients, and vice versa.

As used herein, the term effective amount will refer to an amount of a compound that confers a therapeutic effect on the treated subject. The effect may be objective (i.e. measurable by some test or marker) or subjective (i.e. the subject gives an indication of and/or feels an effect).

For example, referring to the tests described hereinabove, the subject being treated may display an improvement (decrease) of at least about 2 points, such as at least about 3 points, for example at least about 5 points (e.g at least about 10 points) on the ESS; and/or an improvement (increase) of at least about 2 points, such as at least about 3 points, for example at least about 5 points (e.g at least about 10 points) on the FOSQ (total score); and/or an improvement (decrease) of at least about 3 points, such as at least about 4 points, for example at least about 5 points (e.g at least about 10 points) on an MFI scale. For the avoidance of doubt, all improvements in score listed in this paragraph refer to the total score achieved on the test and may be relative to the subject's score achieved prior to the commencement of the treatment.

Wherever the word "about" is employed herein, it will be appreciated that such variables are approximate and as such may vary by ±10%, for example ±5%, or ±2% (e.g. ±1%) from the numbers specified.

Certain hypersomnolence disorders are understood to be influenced by γ-aminobutyric acid (GABA) receptor signalling in the central nervous system (CNS); in particular, positive modulation of the ionotropic $GABA_A$ receptor. Such disorders may collectively be referred to as $GABA_A$ receptor-mediated hypersomnia. In certain embodiments of the invention, the hypersomnolence is $GABA_A$ receptor-mediated hypersomnia.

Hypersomnolence disorders may involve positive allosteric modulation of $GABA_A$ receptors by an endogenous substance present at elevated levels in the cerebrospinal fluid (CSF) of patients displaying symptoms of hypersomnolence. The CSF of a hypersomnolent subject may have elevated levels of an endogenous positive allosteric modulator of $GABA_A$ receptors relative to the cerebrospinal fluid of a subject without hypersomnolence.

In one embodiment of the invention, the sleep disorder may be classified and diagnosed according to the the International Classification of Sleep Disorders $3^{rd}$ Edition (ISCD-3) classification (as of 6 Jun. 2016).

In another embodiment of the invention, hypersomnolence may be primary hypersomnia or secondary hypersomnia.

Hypersomnia is judged to be "secondary" if it is caused by a problem with night time sleep, inability to get enough sleep, or other medical problems that result in sleepiness. For example, patients with obstructive sleep apnea, who have multiple interruptions in breathing throughout the night, are frequently sleepy during the day, but their hypersomnia is judged to be secondary to their sleep apnea. Secondary hypersomnia can be triggered by infections, depression, kidney failure, chronic fatigue syndrome, and neurodegenerative diseases such as Parkinson's disease and myotonic dystrophy.

The primary hypersomnias, in contrast, occur in the absence of such medical problems and despite normal quality and quantity of night time sleep (and sometimes despite exceptionally long periods of night time sleep). The primary hypersomnias are thought to arise from problems with the brain's systems that regulate sleep and wake.

In a further aspect of the invention, the hypersomnolence is primary hypersomnia.

In yet another aspect of the invention, the hypersomnolence is secondary hypersomnia.

In particular embodiments, the hypersomnolence is a disorder selected from the group consisting of idiopathic hypersomnia, recurrent hypersomnia, narcolepsy, shift work sleeping disorder, excessive sleepiness, endozepine-related recurrent stupor, amphetamine-resistant hypersomnia.

In one embodiment of the present invention, the hypersomnolence disorder is a $GABA_A$-receptor mediated hypersomnia.

In a further embodiment of the present invention, the hypersomnolence disorder is idiopathic hypersomnia.

The skilled person will appreciate that idiopathic hypersomnia (IH) refers to a disorder principally characterised by chronic excessive day time sleepiness over an extended period of time, wherein the subject typically displays symptoms constantly, or near constantly. IH displays some similarity to narcolepsy; however, the symptoms of cataplexy, paralysis and REM during the onset of sleep are not typically associated with IH. The disorder is described as idiopathic because historically it has been difficult for clinicians to determine a cause.

In contrast to subjects suffering from idiopathic hypersomnia, patients with recurrent hypersomnia typically experience periods of excessive daytime sleepiness lasting from one to several days interspersed with periods where they do not display any symptoms of hypersomnia.

In a further embodiment, the hypersomnolence disorder is recurrent hypersomnia.

The skilled person will appreciate that narcolepsy indicates a neurological disorder characterised by the brain's inability to control the sleep/wakefulness cycle. Subjects with narcolepsy suffer from chronic daytime sleepiness and episodes in which they fall asleep unexpectedly during the day. These 'sleep attacks' can occur at any time and during any activity. For example, attacks may occur during school or work hours, while eating, playing sports or while driving. Symptoms of narcolepsy include cataplexy, paralysis and REM during the onset of sleep.

As used herein, the term "narcolepsy" includes both type 1 narcolepsy (with cataplexy) and type 2 narcolepsy (without cataplexy).

In certain embodiments, the hypersomnolence disorder is type 1 narcolepsy.

In further certain embodiments, the hypersomnolence disorder is type 2 narcolepsy.

In certain other embodiments, the hypersomnolence disorder is shift work sleeping disorder.

In certain other embodiments, the hypersomnolence disorder is excessive sleepiness.

In certain other embodiments, the hypersomnolence disorder is endozepine-related recurrent stupor.

In certain other embodiments, the hypersomnolence disorder is amphetamine-resistant hypersomnia.

In certain further embodiments, the hypersomnolence is related to a disorder selected from the group consisting of restless leg syndrome, nocturnal dystonia, nocturnal movement disorder, Klein-Levin syndrome, Parkinson's disease, a disorder related to a medication or substance, a psychiatric disorder, rapid eye movement (REM) behaviour disorder, frontal nocturnal dystonia, nocturnal movement disorder, obstructive sleep apnoea, liver cirrhosis and hepatic encephalopathy.

In another aspect of the invention, there is provided a method of promoting wakefulness comprising administering an effective amount of 3α-ethynyl-3β-hydroxy-5α-androstan-17-one oxime, or a pharmaceutically acceptable salt thereof, to a subject in need thereof.

As used herein, the phrase "promoting wakefulness" may be understood to indicate delaying the onset of sleep, and includes the prophylactic treatment of hypersomnolence (for example, the prophylaxis of the specific disorders listed herein). The phrase may also be understood to indicate the promotion and maintenance of an alert state, for example as determined by any of the subjective or objective assessments described herein, or as subjectively experienced by the subject.

The skilled person will understand that the terms prevention (and, similarly, preventing) when used herein take their normal meanings in the art. In particular, these terms may refer to achieving a reduction in the likelihood of developing the relevant condition (for example, a reduction of at least 10% when compared to the baseline level, such as a reduction of at least 20% or, more particularly, a reduction of at least 30%). Similarly, the term preventing may also be referred to as prophylaxis, and vice versa.

The skilled person will understand that references to a subject in need thereof refer to a therapeutic use.

Alternatively, in certain instances, the phrase "promoting wakefulness" may encompass a non-therapeutic promotion of wakefulness.

Accordingly, in another aspect of the invention, there is provided a method of promoting wakefulness comprising administering an effective amount of 3α-ethynyl-3β-hydroxy-5α-androstan-17-one oxime, or a pharmaceutically acceptable salt thereof, to a subject.

In an alternative aspect of the invention, there is provided the use of 3α-ethynyl-3β-hydroxy-5α-androstan-17-one oxime, or a pharmaceutically acceptable salt thereof, in promoting wakefulness.

In particular embodiments of the method and use of these aspects of the invention, the reference to promoting wakefulness will also refer to the prevention of (i.e. prophylaxis of) hypersomnolence (as defined herein).

Compounds of the invention will normally be administered orally, intravenously, subcutaneously, buccally, rectally, dermally, nasally, tracheally, bronchially, sublingually, intranasally, topically, by any other parenteral route or via inhalation, in a pharmaceutically acceptable dosage form.

Compounds of the invention may be administered alone or may be administered by way of known pharmaceutical compositions/formulations, including tablets, capsules or elixirs for oral administration, suppositories for rectal administration, sterile solutions or suspensions for parenteral or intramuscular administration, and the like.

In certain embodiments, the compounds of the invention are administered in the form of a pharmaceutical composition, optionally in admixture with one or more pharmaceutically acceptable adjuvant, diluent or carrier.

In another aspect of the invention, there is provided a method of treating hypersomnolence or promoting wakefulness as defined hereinabove, which comprises administering a therapeutically effective amount of a pharmaceutical composition comprising 3α-ethynyl-3β-hydroxy-5α-androstan-17-one oxime, or a pharmaceutically acceptable salt thereof, optionally in admixture with one or more pharmaceutically acceptable adjuvant, diluent or carrier, to a subject in need thereof.

Compounds of the invention may also be combined with one or more other (i.e. different) therapeutic agents that are useful in the treatment of hypersomnolence and/or promoting wakefulness. Such combination products that provide for the administration of a compound of the invention in conjunction with one or more other therapeutic agent may be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the one or more other therapeutic agent).

The skilled person will understand that references herein to compounds of the invention being for particular uses (and, similarly, to uses and methods of use/treatment) may also apply to pharmaceutical compositions, comprising compounds of the invention as described herein.

The physician, or the skilled person, will be able to determine the actual dosage which will be most suitable for an individual patient, which is likely to vary with the route of administration, the type and severity of the condition that is to be treated, as well as the species, age, weight, sex, renal function, hepatic function and response of the particular patient to be treated.

The methods of treatment, compounds for use, uses and compositions described herein may have the advantage that they may enable treatment of disorders for which no treatment currently exists and/or may be more efficacious than, be less toxic than, be longer acting than, be more potent than, produce fewer side effects than, treatments known in the art for the above-stated indications.

Preparation of Compounds/Compositions

Pharmaceutical compositions/formulations, as described herein may be prepared in accordance with standard and/or accepted pharmaceutical practice.

Thus, in a further aspect of the invention there is provided a process for the preparation of a pharmaceutical composition/formulation, as hereinbefore defined, which process comprises bringing into association a compound of the invention, as hereinbefore defined, with one or more pharmaceutically-acceptable adjuvant, diluent or carrier.

Compounds of the invention may be prepared in accordance with techniques that are well known to those skilled in the art, such as those described in the examples provided hereinafter.

EXAMPLES

The invention is further illustrated, but not limited, by the following examples.

Example 1. Synthesis of 3α-ethynyl-3β-hydroxy-5α-androstan-17-one Oxime

3α-Ethynyl-3β-hydroxy-5α-androstan-17-one oxime may be prepared according to the method disclosed in WO 2008/063128.

Step 1: Synthesis of 3α-ethynyl-3β-hydroxy-5α-androstan-17-one

5α-Androstan-3,17-dione (5.0 mmol) was dissolved in 50 mL dry THF at room temperature (rt) under nitrogen. Ethynyl magnesium bromide (1.1 equiv) was added dropwise at rt under stirring and the solution was left stirring overnight at rt under nitrogen flow. The solution was then quenched with saturated $NH_4Cl_{(aq)}$ and the aqueous phase extracted with dichloromethane (3×30 mL). The collected organic phases were evaporated under reduced pressure, the resulting yellow oil dissolved in dichloromethane, washed with brine and dried over $MgSO_4$. The solution was reduced under vacuum, and the residue purified by silica flash column chromatography (1:4 diethylether:dichloromethane), typical yields 65%. Eventual traces of byproducts can be eliminated by further recrystallization from diethylether.

$^1$H NMR (400 MHz, $CDCl_3$): $\delta_H$ 2.43 (s, 1H); 2.42 (m, 1H); 2.10-2.04 (m, 2H); 1.02 (m, 1H); 0.86 (s, 3H); 0.83 (s, 3H).

Step 2: Synthesis of 3α-ethynyl-3β-hydroxy-5α-androstan-17-one Oxime

3α-Ethynyl-3β-hydroxy-5α-androstan-17-one (10 mmol) was dissolved in dichloromethane 5 mL and ethanol 50 mL at room temperature and air atmosphere, in a 250 mL round bottom flask. 4 equiv. of $NH_2OH$ hydrochloride and 4 equiv. of sodium acetate were dissolved in 5 mL $H_2O$ and then added to the steroid solution. 20 mL of ethanol was added and the mixture put on reflux overnight. The mixture was then cooled and the solvent removed under reduced pressure. The white residue was treated with 50 mL $H_2O$ and 50 mL dichloromethane, the aqueous phase extracted with 3×30 mL dichloromethane. The collected organic phases were then dried over $MgSO_4$, filtrated and the solvent removed under reduced pressure. The final residue was purified by silica flash column chromatography dichloromethane:diethyl ether 4:1, typical yields 95-100% (quantitative).

$^1$H NMR (400 MHz, $CDCl_3$): $\delta_H$ 2.51-2.47 (m, 2H); 2.48 (s, 1H); 1.00 (m, 1H); 0.80 (m, 1H); 0.90 (s, 3H); 0.83 (s, 3H).

Example 2. Effect of 3α-ethynyl-3β-hydroxy-5α-androstan-17-one Oxime on the Positive Allosteric Modulation of $GABA_A$ Receptors by CSF and/or Plasma Obtained from Patients Displaying Symptoms of Hypersomnolence 3α-Ethynyl-3β-hydroxy-5α-androstan-17-one oxime is tested as an antagonist of excessive $GABA_A$ receptor enhancement by CSF and/or plasma from patients with hypersomnia. HEK-293 cell lines stably expressing a functional recombinant human α1β2γ2 $GABA_A$ receptor or a human $GABA_A$ receptor with other subunit combination are studied by whole cell patch clamp. Cells in extracellular solution, in mM: 137 NaCl, 5.0 KCl, 1.0 $CaCl_2$, 1.2 $MgCl_2$, 10 glucose, 10 HEPES-NaOH pH 7.4, are for predefined time periods (typically 40 ms-2 s, depending on receptor subtype) exposed to GABA, followed by GABA+CSF, and followed by GABA+CSF+3α-ethynyl-3β-hydroxy-5α-androstan-17-one oxime. During measurements a typical electrode resistance is 2-6 MΩ when filled with intracellular solution, in mM: 140 Cs-gluconate, 3.0 NaCl, 1.2 $MgCl_2$, 1.0 EGTA, 2 Mg-ATP, 10 HEPES-CsOH pH 7.2.

Example 3. Clinical Study of 3α-ethynyl-3β-hydroxy-5α-androstan-17-one Oxime in Idiopathic Hypersomnia (IH) Patients A study to assess the preliminary efficacy of 3α-ethynyl-3β-hydroxy-5α-androstan-17-one oxime in male and female patients with IH will be performed.

Study Design

Double-blind, randomized, placebo-controlled crossover phase 2a study to assess the efficacy of multiple oral doses of 3α-ethynyl-3β-hydroxy-5α-androstan-17-one oxime in patients with IH. Patients will be randomized (1:1) to one of two study arms:

I. 3α-Ethynyl-3β-hydroxy-5α-androstan-17-one oxime/washout/placebo

II. Placebo/washout/3α-ethynyl-3β-hydroxy-5α-androstan-17-one oxime

Objectives and Endpoints

Objective

The objective is to evaluate the efficacy of 3α-ethynyl-3β-hydroxy-5α-androstan-17-one oxime after multiple dose administration in patients with IH.

Endpoints

The following efficacy endpoints will be used:

Intraindividual comparison of change in Epworth Sleepiness Scale (ESS) from baseline to day 14 in 3α-ethynyl-3β-hydroxy-5α-androstan-17-one oxime treated patients versus change in ESS from baseline to day 14 in placebo treated patients.

Intraindividual comparison of change in Maintenance of Wakefulness Test (MWT) from baseline to day 14 in 3α-ethynyl-3β-hydroxy-5α-androstan-17-one oxime treated patients versus change in MWT from baseline to day 14 in placebo treated patients.

Intraindividual comparison of change in Clinical Global Impression scale (CGI) from baseline to day 14 in 3α-ethynyl-3β-hydroxy-5α-androstan-17-one oxime treated patients versus change in CGI from baseline to day 14 in placebo treated patients.

Intraindividual comparison of change in Karolinska Sleepiness scale (KSS) from baseline to day 14 in 3α-ethynyl-3β-hydroxy-5α-androstan-17-one oxime treated patients versus change in KSS from baseline to day 14 in placebo treated patients.

A total of 14 patients with IH will be enrolled in the part B study in order to achieve at least 12 evaluable patients. At least five patients of each gender should be enrolled. Withdrawn patients will not be replaced.

Study Population and Inclusion Criteria

Male and female patients 18 to 55 years with a diagnosis of IH.

For inclusion in the study subjects must fulfil the following criteria:

Males or females age 18 to 55 years, who meet the International Classification of Sleep Disorders criteria 3$^{rd}$ edition (ICSD-3) for the diagnosis of IH within the last 6 months with the following exception: a Multiple Sleep Latency Test (MSLT) of less than 8 minutes is required for all patients. These diagnostic outputs must be documented.

Epworth Sleepiness Scale (ESS) of 11 or greater.

An apnea-hypopnea index (AHI)<15 within the last 6 months.

Patients on current treatment for their hypersomnolence disorder may be enrolled after discontinuing the medication and a washout phase (at least five times the half-life of the medication but not less than 14 days).

Fertile female patients, willing to use a non-hormonal intrauterine device (IUD) or condom together with a medically accepted method of birth control (diaphragm, sponge, cervical cap) or sexual abstinence and agree to continue the use of this method for the duration of the trial and thereafter for one month after the last dosing of the Investigational Medicinal Product (IMP).

Fertile male subjects must be willing to use condoms and refrain from donating sperm and ensure that their fertile female partners are using contraceptive methods to prevent pregnancy (as described in inclusion criterion above) for the duration of the trial and thereafter for one month after the last dosing of the IMP.

Women who are surgically sterile or two years post-menopausal may be included without fulfilling the above criteria on birth control.

Men who are surgically sterile may be included without they/their partner fulfilling the above criteria on birth control.

Women must supply a negative urine pregnancy test on day 0 prior to IMP intake

Exclusion Criteria

Subjects must not be included in the study if any of the following exclusion criteria are fulfilled:

History of pathological electroencephalography (EEG).

Pathological electrocardiography (ECG) at screening.

Inability to swallow the required number of study medication capsules or to otherwise comply with study procedures.

Any concurrent illness which at the discretion of the Investigator would compromise patient safety and/or compromise the objectives outlined in the protocol. These could include, but are not limited to, cardiovascular, endocrine, neoplastic, gastrointestinal, hematologic, hepatic, immunologic, metabolic, neurological (other than narcolepsy/hypersomnia), psychiatric (including, but not limited to, depression and anxiety), pulmonary, and/or renal disease.

Women with significant premenstrual syndrome (PMS) including PMS hypersomnolence.

Women diagnosed with menstrual related hypersomnia.

History of severe allergy/hypersensitivity or on-going allergy/hypersensitivity, as judged by the Investigator, or history of hypersensitivity to drugs with a similar chemical structure or class to 3α-ethynyl-3β-hydroxy-5α-androstan-17-one oxime.

Current or recent (within one year) history of use of drugs of abuse including alcohol, anabolic steroids or as defined by the DSM-IV (Diagnostic and Statistical Manual of Mental Disorders).

Positive screen for drugs of abuse at screening or at baseline prior to administration of the study treatment.

Female patients who are pregnant or nursing.

Abnormal renal or hepatic function as reflected by a serum creatinine>2.0 mg/dL (177 micromol/L) or abnormal liver biochemical tests (AST or ALT>2× upper limit of normal), serum bilirubin or INR>1.5× upper limit of normal.

Evidence of active chronic viral infection including hepatitis B (serum hepatitis B surface antigen positive), hepatitis C (e.g. HCV RNA positive), and/or Human Immunodeficiency Virus (HIV positive).

Have an occupation that requires variable shift work or routine night shift.

Participation in any other clinical study that included drug treatment with the last administration within the past 30 days or five half-lives (whichever is longer) prior to administration of study treatment in this study. Patients consented and screened but not dosed in previous clinical studies are not excluded.

Use of hypnotics, stimulants, tranquilizers, antihistamines (except for non-sedating antihistamines), benzodiazepines or clonidine at the start of the baseline period or during the study. Patients taking anticonvulsants are not eligible to participate even if they are willing to washout anticonvulsants for the trial.

Use of over the counter (OTC), prescription medications or off label medications for hypersomnolence disorders must be discontinued at least five times the half-life of the medication but not less than 14 days prior to baseline.

Regular or recent (i.e. within 14 days prior to enrolment) use of any prescribed or non-prescribed medications which, at the discretion of the Investigator, might compromise safe patient participation in the study and/or interpretation of the study results.

Unsuitable for the study as judged by Investigator.

Overall Description of Study Design

The study will be conducted at specialised sleep research centres.

Consenting patients will be screened for eligibility according to the study-specific inclusion/exclusion criteria within four weeks prior to the (first) administration of study treatment. All patients enrolled in the study should fulfil the ICSD-3 criteria for IH. The diagnosis is either done during screening or if available from the last 6 months (if medical records are available for verification). All patients should have done at least one documented MSLT either during screening or during the previous diagnostic assessment (within last 6 months). Any OTC, prescription or off label medications for hypersomnolence disorders must be discontinued at least 14 days prior to baseline.

Eligible patients will be randomized on Day 1 to receive either treatment order (3α-ethynyl-3β-hydroxy-5α-androstan-17-one oxime/placebo or placebo/3α-ethynyl-3β-hydroxy-5α-androstan-17-one oxime). Each intervention is administered once or twice daily for 14 consecutive days (3α-ethynyl-3β-hydroxy-5α-androstan-17-one oxime or placebo). Each patient will receive the same dose of 3α-ethynyl-3β-hydroxy-5α-androstan-17-one oxime twice daily. There is a one week washout period between the two interventions when patients are administered placebo capsules in a single blind manner. There will be a follow-up visit 14 days after the last dose of study treatment.

The patients will be randomised sequentially as they are coming for the baseline/randomisation visit. The treatment order is double-blind, i.e. it will not be disclosed to the subjects, site staff or Sponsor. The study runs for 35 days with primary assessments to be done at baseline and at the end of each two-week treatment period. Selected assessments are also done after one week per intervention. There will be a follow-up visit 14 days after the last treatment visit.

Dosage and Mode of Administration

3α-ethynyl-3β-hydroxy-5α-androstan-17-one oxime will be supplied as a solid in hard gelatine capsules (size 0) intended for oral administration. Each capsule contains 10 mg 3α-ethynyl-3β-hydroxy-5α-androstan-17-one oxime and pharmaceutically-acceptable excipient(s).

Placebo capsules will contain the excipient(s) and be of identical appearance to the 3α-ethynyl-3β-hydroxy-5α-androstan-17-one oxime capsules. The number of placebo capsules to be administered will be adjusted to match the number of 3α-ethynyl-3β-hydroxy-5α-androstan-17-one oxime capsules.

3α-Ethynyl-3β-hydroxy-5α-androstan-17-one oxime will be administered once or twice daily for 14 consecutive days. Each patient will receive the same dose of 3α-ethynyl-3β-hydroxy-5α-androstan-17-one oxime. Also, the placebo will be administered for 14 consecutive days. The order of administering 3α-ethynyl-3β-hydroxy-5α-androstan-17-one versus placebo will be randomised.

All patients will also receive placebo capsules during the washout at days 15 to 21 in a single blind manner.

Duration of Patients' Involvement in the Study

Patients will be screened for eligibility according to study-specific inclusion/exclusion criteria within 28 days prior to start of study treatment (i.e. Baseline 1). The study is approx. 35 days with a follow-up visit 14 days after last administration of IMP. Hence, in total up to approximately 77 days.

Efficacy Assessments
ESS
MWT
CGI
Actigraphy (multiple variables)
Sleep wake diary
Karolinska Sleepiness scale
Statistical Methods All statistical calculations will be performed using SAS® software (SAS Institute Inc., Cary, N.C., USA) or equivalent program. The statistical analyses will include descriptive statistics reflecting the exploratory nature of the study. In general, the data will be presented by treatment arm.

Continuous data will be summarised by treatment arm using number, arithmetic mean, standard deviation (SD), median, minimum and maximum. Categorical data will be summarised by dose using the number and percentage of patients in each category.

Unless otherwise stated, statistical evaluations will be based on the Full Analysis Set (FAS), defined as all patients who have received study treatment and have baseline and post baseline data from both study arms. Evaluations will be done according to actual treatment regardless of randomization. The FAS data set will be used for preliminary efficacy analyses.

The Per Protocol Analysis Set (PPAS) comprises data from all patients randomized and treated with efficacy data who are compliant with investigational product administration and study procedures; i.e. patients with no major protocol deviations, which will be defined prior to unblinding. The PPAS will be used for analysis of efficacy endpoints.

The invention claimed is:

1. A method for the treatment of hypersomnolence, comprising administering a therapeutically effective amount of 3α-ethynyl-3β-hydroxy-5α-androstan-17-one oxime,

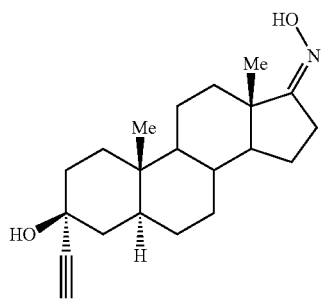 [SMILES: C#C[C@]1(O)CC[C@]2(C)C3CC[C@]4(C)/C(=N\O)CCC4C3CC[C@H]2C1]

or a pharmaceutically acceptable salt thereof, to a subject in need of such treatment.

2. The method as claimed in claim 1, wherein the hypersomnolence is $GABA_A$ receptor-mediated hypersomnia.

3. The method as claimed in claim 1, wherein the hypersomnolence is primary hypersomnia.

4. The method as claimed in claim 1, wherein the hypersomnolence is secondary hypersomnia.

5. The method as claimed in claim 1, wherein the hypersomnolence is a disorder selected from the group consisting of idiopathic hypersomnia, recurrent hypersomnia, narcolepsy, shift work sleeping disorder, endozepine induced-recurrent stupor and amphetamine-resistant hypersomnia.

6. The method as claimed in claim 1, wherein the hypersomnolence disorder is idiopathic hypersomnia.

7. The method as claimed in claim 1, wherein the hypersomnolence disorder is type 2 narcolepsy.

8. The method as claimed in claim 1, wherein the hypersomnolence disorder is type 1 narcolepsy.

9. The method as claimed in claim 1, wherein the hypersomnolence is induced by a disorder selected from the group consisting of restless leg syndrome, nocturnal dystonia, nocturnal movement disorder, Klein-Levin syndrome, Parkinson's disease, a disorder caused by a medication or substance, a psychiatric disorder, rapid eye movement (REM) behaviour disorder, frontal nocturnal dystonia, nocturnal movement disorder, obstructive sleep apnoea, liver cirrhosis and hepatic encephalopathy.

10. The method as claimed in claim 1, wherein 3α-ethynyl-3β-hydroxy-5α-androstan-17-one oxime is administered in the form of a pharmaceutical composition, optionally in admixture with one or more pharmaceutically acceptable adjuvants, diluents or carriers.

* * * * *